(12) United States Patent
Aggerholm

(10) Patent No.: US 10,046,145 B2
(45) Date of Patent: Aug. 14, 2018

(54) BALLOON CATHETER AND METHOD OF MAKING SAME

(71) Applicant: Cook Medical Technologies LLC, Bloomington, IN (US)

(72) Inventor: Steen Aggerholm, Store Heddinge (DK)

(73) Assignee: Cook Medical Technologies LLC, Bloomington, IN (US)

( * ) Notice: Subject to any disclaimer, the term of this patent is extended or adjusted under 35 U.S.C. 154(b) by 506 days.

(21) Appl. No.: 14/526,725

(22) Filed: Oct. 29, 2014

(65) Prior Publication Data

US 2015/0157834 A1   Jun. 11, 2015

Related U.S. Application Data

(60) Provisional application No. 61/914,446, filed on Dec. 11, 2013.

(51) Int. Cl.
*A61M 25/10*   (2013.01)
*A61M 25/00*   (2006.01)

(52) U.S. Cl.
CPC .... *A61M 25/1025* (2013.01); *A61M 25/1006* (2013.01); *A61M 25/1034* (2013.01); *A61M 25/0015* (2013.01); *A61M 25/0032* (2013.01); *A61M 2025/004* (2013.01); *Y10T 156/1056* (2015.01)

(58) Field of Classification Search
CPC ............ A61M 25/1025; A61M 25/004; A61M 2025/004; Y10T 156/1056; Y10T 156/1062
See application file for complete search history.

(56) References Cited

U.S. PATENT DOCUMENTS

| 5,217,482 A | 6/1993 | Keith | |
|---|---|---|---|
| 6,403,011 B1 * | 6/2002 | Stamberg | A61M 25/001 156/250 |
| 7,351,301 B2 * | 4/2008 | Lumauig | A61M 25/1006 156/272.2 |
| 2005/0065544 A1 * | 3/2005 | Yamaguchi | A61M 25/0029 606/192 |
| 2008/0039784 A1 * | 2/2008 | Quinn | A61M 25/0029 604/96.01 |
| 2009/0171277 A1 | 7/2009 | Pepper | |
| 2012/0303054 A1 * | 11/2012 | Wilson | A61M 25/0009 606/194 |

FOREIGN PATENT DOCUMENTS

EP     0268068     10/1986

* cited by examiner

*Primary Examiner* — Mark A Osele
*Assistant Examiner* — Christopher C Caillouet
(74) *Attorney, Agent, or Firm* — Liell + McNeil

(57) ABSTRACT

A balloon catheter includes a one-piece extrusion having inner and outer tubular walls, where the inner tubular wall defines a wire guide lumen, and a clearance extending between the inner and outer tubular walls forms an inflation lumen. A balloon is attached to the outer tubular wall and to the inner tubular wall, such that the inflation lumen is in fluid communication with the balloon and the wire guide lumen extends through the balloon. A method of making the balloon catheter is also disclosed.

13 Claims, 3 Drawing Sheets

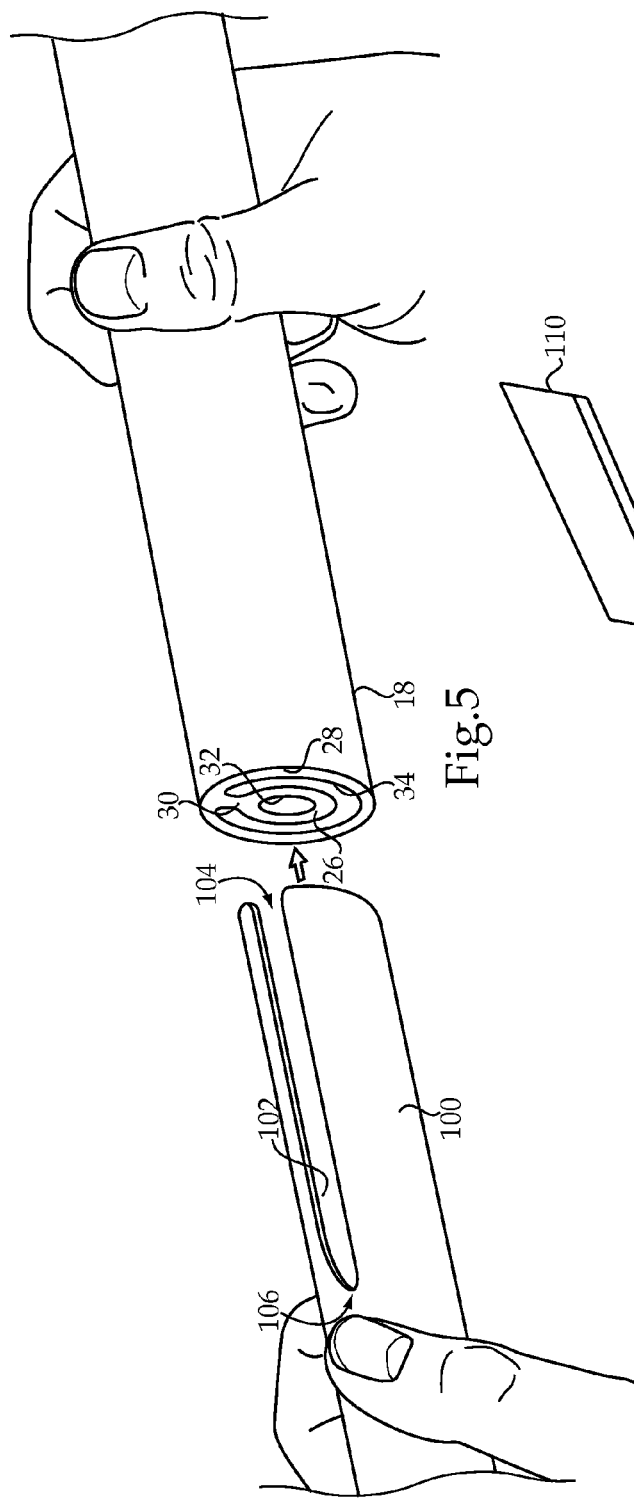
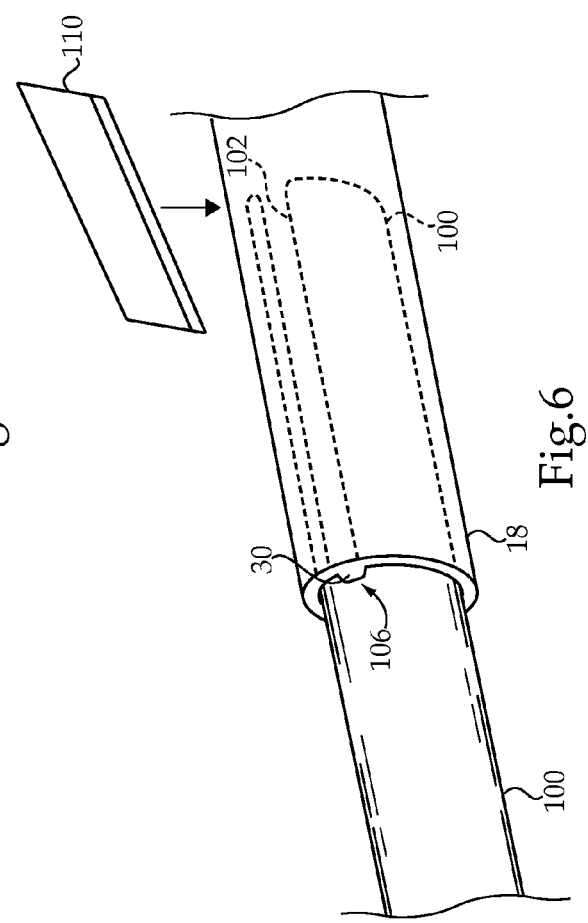
Fig.5
Fig.6

BALLOON CATHETER AND METHOD OF MAKING SAME

TECHNICAL FIELD

The present disclosure relates generally to a balloon catheter, and more particularly to a balloon catheter made from a one-piece extrusion having attached inner and outer tubular walls.

BACKGROUND

Balloon catheters are used in a variety of different medical procedures, notably in the field of peripheral intervention. A typical balloon catheter includes an elongate body or shaft having an inflatable balloon attached near a distal end thereof. An inflation fluid is supplied via a longitudinally extending lumen in the shaft to inflate the balloon for purposes such as deforming blockages in veins or arteries, expanding implantable devices such as stents, and blocking fluid flow through body lumens. A second lumen is often provided through at least a portion of the balloon catheter, such that the device can be slid over a wire guide to a location of interest within a patient.

It is common for balloon inflation lumens and wire guide lumens in a balloon catheter to be formed by separate tubular elements that are attached to one another via adhesives and the like. Manufacturing balloon catheters can be relatively labor intensive given the need to attach a number of different parts, some of which can be quite small. European Patent Application Publication No. 0268068 to Marangoni discloses one example angioplasty catheter, where two coaxial lumens are formed in separate tubes attached to one another, and a balloon is attached to both the outer tube and the inner tube, providing both an outer inflation lumen and an inner lumen for the apparent purpose of guiding the device over a wire guide or the like. While Marangoni may work suitably in its intended environment, there is always room for improvement, particularly with regard to ease of manufacturing and design complexity.

SUMMARY OF THE DISCLOSURE

In one aspect, a method of making a balloon catheter includes holding a one-piece extrusion including an inner tubular wall, and outer tubular wall extending circumferentially around the inner tubular wall, and a longitudinally extending connecting wall attaching the inner and outer tubular walls. The method further includes cutting circumferentially through the outer tubular wall and longitudinally through the connecting wall so as to detach a portion of the outer tubular wall from the one-piece extrusion. The method further includes attaching a proximal end of a balloon to the outer tubular wall and a distal end of the balloon to the inner tubular wall, after detaching the portion, and such that a first lumen formed by both the inner and outer tubular walls is in fluid communication with the balloon for inflating the same, and a second lumen formed by the inner tubular wall extends longitudinally through the balloon for guiding the balloon catheter over a wire guide.

In another aspect, a balloon catheter includes a manifold defining a first lumen inlet and a second lumen inlet, and a one-piece extrusion defining a longitudinal axis extending between a proximal extrusion end attached to the manifold, and a distal extrusion end. The one-piece extrusion includes an inner tubular wall, an outer tubular wall extending circumferentially around the inner tubular wall, and a connecting wall attaching the inner and outer tubular walls. The inner tubular wall has a wire guide lumen formed therein and in fluid communication with the first lumen inlet, and a clearance extends between the inner and outer tubular walls and forms an inflation lumen in fluid communication with the second lumen inlet. The inner tubular wall has a first length and the outer tubular wall has a second length less than the first length, such that the outer tubular wall has an axial end surface located between the proximal and distal extrusion ends, and the inner tubular wall forms the distal extrusion end. The balloon catheter further includes a balloon having a proximal balloon end attached to the outer tubular wall on a proximal side of the axial end surface, and a distal balloon end attached to the inner tubular wall on a distal side of the axial end surface, such that the inflation lumen is in fluid communication with the balloon, and the inner tubular wall and wire guide lumen extend through the balloon, for guiding the balloon catheter over a wire guide.

BRIEF DESCRIPTION OF THE DRAWINGS

FIG. 5 is a diagrammatic view of an extrusion and a form at one stage of making a balloon catheter, according to one embodiment;

FIG. 6 is a diagrammatic view of the extrusion and form at another stage of making a balloon catheter;

DETAILED DESCRIPTION

Figure 1:
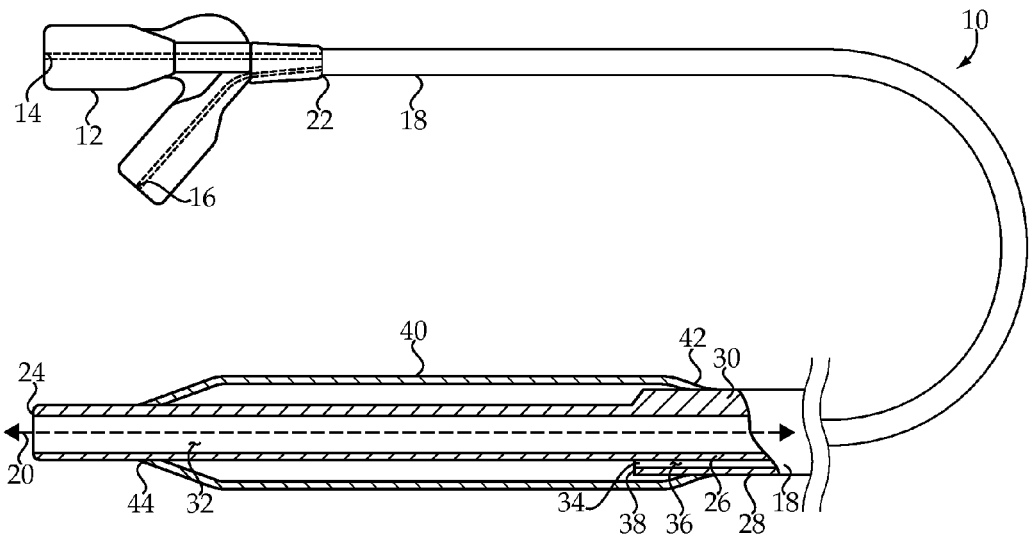
FIG. 1 is a partially sectioned side diagrammatic view of a balloon catheter, according to one embodiment.

Referring to FIG. 1, there is shown a balloon catheter 10 according to one embodiment. Catheter 10 includes a manifold 12 defining a first lumen inlet 14 and a second lumen inlet 16. Catheter 10 further includes a one-piece extrusion 18 defining a longitudinal axis 20 extending between a proximal extrusion end 22 attached to the manifold, and a distal extrusion end 24. Extrusion 18 further includes an inner tubular wall 26, an outer tubular wall 28 extending circumferentially around inner tubular wall 26, and a connecting wall 30 attaching inner and outer tubular walls 26 and 28. Those skilled in the art will be familiar with the extrusion of tubular elements of various form for use in constructing medical devices. Extrusion 18 will be extruded in a generally conventional manner from a conventional extrusion die, and has a uniform material composition throughout, in contrast to co-extruded components and of course components made via the attachment of multiple separate extrusions. Extrusion 18 will thus typically be free of seams, adhesives, boundaries and nonuniformities that can result from attachment of separate molded elastomeric elements. In a practical implementation strategy, extrusion 18 may be nylon, but a variety of other suitable polymers known in the art might be used. As will be further apparent from the following description, the geometry of extrusion 18 enables its processing during the making of balloon catheter 10 in a manner that is relatively rapid, reliable and economical.

Inner tubular wall 26 may have a first or wire guide lumen 32 formed therein and in fluid communication with first lumen inlet 14. A clearance 34 extends between inner tubular wall 26 and outer tubular wall 28 and forms a second or inflation lumen 36 in fluid communication with second lumen inlet 26. Wire guide lumen 32 and inflation lumen 36 are fluidly separate from one another, and will typically be substantially coaxial. Inner tubular wall 26 has a first length and outer tubular wall 28 has a second length less than the first length, such that outer tubular wall 28 has an axial end surface 38 located between proximal and distal extrusion ends 22 and 24. In some embodiments, inner tubular wall 26 might be 3-4 French in size, with outer tubular wall 28 being two to three times as large, however, the present disclosure is not thereby limited. Catheter 10 further includes a balloon 40 having a proximal balloon end 42 attached to outer tubular wall 28 on a proximal side of axial end surface 38. Balloon 40 further has a distal balloon end 44 attached to inner tubular wall 26 on a distal side of axial end surface 38, such that inflation lumen 36 is in fluid communication with balloon 40, in particular with an internal cavity of balloon 40, and further such that inner tubular wall 26 and wire guide lumen 32 extend through balloon 40, for guiding catheter 10 over a wire guide. From FIG. 1 it can be seen that a wire guide advanced through inlet 14 and through wire guide lumen 32 can extend all the way axially through extrusion 18, such that catheter 10 can be guided into the vasculature or another body lumen of interest in a patient in a conventional manner. It can further be seen from FIG. 1 that a source of inflation fluid can be fluidly connected to inlet 16, and used to supply an inflation fluid via inflation lumen 36 into balloon 40, and also for withdrawing that inflation fluid, in a generally conventional manner. Lumen 32 could also be used for injection of a contrast agent, or for still other purposes. As further discussed herein, it is the removal of a portion of outer tubular wall 28 from a base extrusion that enables the fluid connections and general geometry of balloon catheter 10 to be obtained. The use of a one-piece base extrusion as a starting component can minimize the number of processing steps as well as the materials needed for balloon catheter construction.

Figure 2:
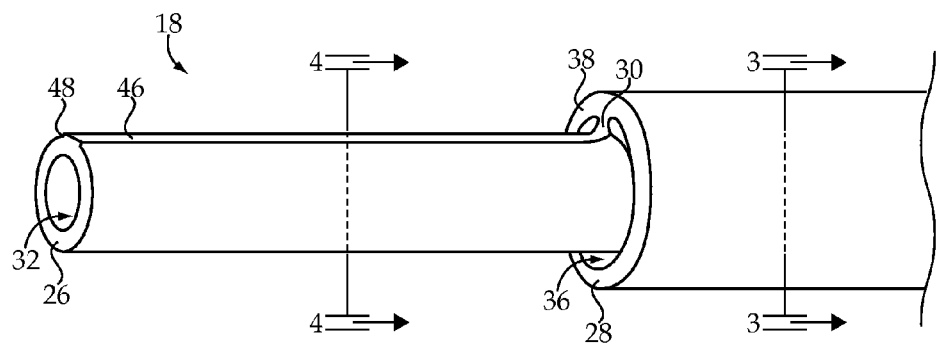
FIG. 2 is a diagrammatic view of an extrusion for use in making a balloon catheter, according to one embodiment.

Referring also now to FIG. 2, there is shown extrusion 18 as it might appear prior to being assembled with manifold 12 and balloon 40. A portion of outer tubular wall 28 has been removed, and moving to the left in FIG. 2 outer tubular wall 28 terminates at exposed axial end surface 38, such that inner tubular wall 26 extends distally past axial end surface 38. In FIG. 2, connecting wall 30 is shown attaching outer tubular wall 28 and inner tubular wall 26. Detaching a portion of outer tubular wall 28 during making catheter 10 may include removal of material of extrusion 18 forming part of outer tubular wall 28, and also material forming part of connecting wall 30. Also visible in FIG. 2 is a longitudinally extending planar surface 46 that is a result of longitudinally cutting through wall 30 via a blade as further discussed herein. It may be noted that planar surface 46 renders an axial cross sectional profile of inner tubular wall 26 non-uniform. In other words, while an outer circumferential profile of outer tubular wall 28 may be circular, and an outer circumferential profile of inner tubular wall 26 may be mostly circular, the circularity of inner tubular wall 26 may be interrupted by planar surface 46. In one practical implementation strategy, planar surface 46 is elevated slightly from an exterior of inner tubular wall 26, and located on a longitudinally extending spine 48. Stated another way, surface 46 may be understood not to be a part of inner tubular wall 26, but instead a part of connecting wall 30 that remains after detaching the segment of outer tubular wall 28, and included upon spine 48. In other embodiments, planar surface 46 might reside on inner tubular wall 26 itself, depending upon the extent to which a height of wall 30 is reduced. In other words, wall 30 may be reduced in height distally of axial end surface 38 such that the material previously forming wall 30 is removed entirely, and planar surface 46 is recessed within a circle defined by an outer surface of inner tubular wall 26. In any event, at least a portion of planar surface 46 will be exposed within balloon 40 when catheter 10 is assembled, with planar surface 46 facing a radially outward direction.

Figure 3:
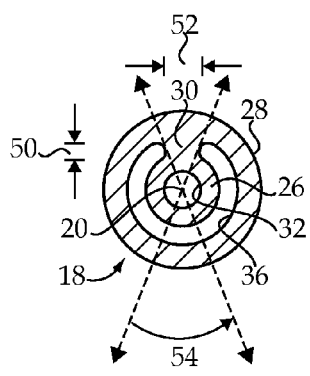
FIG. 3 is a sectioned view taken along line 3-3 of FIG. 2.

Referring also now to FIG. 3, there is shown a sectioned view taken along line 3-3 of FIG. 2. It may be noted from FIG. 3 that wire guide lumen 32 has a circular profile, and inflation lumen 36 has a coaxial C-shaped profile, in the axial section plane. Also shown in FIG. 3 is a radial thickness 50 of connecting wall 30 extending from inner tubular wall 26 to outer tubular wall 28. Connecting wall 30 also has a circumferential thickness 52 greater than radial thickness 50. In a practical implementation strategy, circumferential thickness 52 may be greater than radial thickness 50 by a factor of two or greater. It may further be noted that a first radial thickness of inner tubular wall 26 and a second radial thickness of outer tubular wall 28 appear substantially equal. In other embodiments, the radial thickness of outer tubular wall 28 might be greater than the radial thickness of inner tubular wall 26, two times greater or potentially even more. Such an embodiment might be implemented where balloon 40 is a relatively higher pressure balloon, and a greater wall thickness of outer tubular wall 28 is desired to handle the relatively greater fluid pressure for inflation.

Also shown in FIG. 3 is an angle 54 defined by connecting wall 30 about longitudinal axis 20. In a practical implementation strategy, angle 54 is from about 10° to about 45°, and selected based at least in part upon manufacturing concerns for catheter 10. It will be recalled that a part of outer tubular wall 28 is cut away from the rest of extrusion 18 during manufacturing. To enable a straight line cut through connecting wall 30, leaving planar surface 46, it may be advantageous for connecting wall 30 to have a circumferential width and define an angle 54 such that a straight edged cutting tool such as a razor blade can slice longitudinally through connecting wall 30 without compromising wire guide lumen 32. Those skilled in the art will thus appreciate that a relatively smaller size of angle 54 is consistent with such manufacturing concerns. Angle 54 should nevertheless not be so small that making the extrusion die or successfully extruding material becomes inordinately expensive, nor such that connecting wall 30 is unduly weak or subject to kinking or folding when catheter 10 is coiled for packaging or during use. Catheter 10 may have a flexibility that is uniform through nearly 360° about axis 20, and a relatively small circumferential thickness of wall 30 is consistent with such capabilities.

Figure 4:
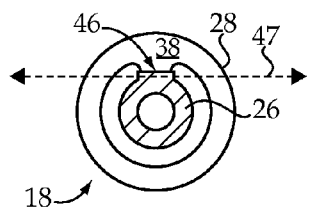
FIG. 4 is a sectioned view taken along line 4-4 of FIG. 2.

Referring also now to FIG. 4, there is shown a sectioned view taken along line 4-4 of FIG. 2. In FIG. 4, axial end surface 38 is visible, and the generally planar shape of surface 46 and its radially outward facing orientation. As noted above, surface 46 may be elevated slightly from the otherwise circular profile of inner tubular wall 26. As also noted above, the cut location through wall 30 might be varied somewhat such that surface 46 is instead formed within a circle defined by inner tubular wall 26. In FIG. 4, a plane 47 is shown through extrusion 18, and it can be noted that were longitudinal cutting through wall 30 to occur at plane 47 then surface 46 would not reside upon a longitudinally extending spine or the like.

INDUSTRIAL APPLICABILITY

Referring to the drawings generally, but in particular now to FIG. 5, there is shown extrusion 18 being held as it might appear prior to being modified for use in making catheter 10. Extrusion 10 is "held" by hand in FIG. 5, but could instead be held in a clamp, fixture, or other part of a device at a processing station. An elongate hollow form 100 is shown held in proximity to extrusion 18, as it might appear just prior to being inserted into clearance 34. Form 100 may be a conventional metallic cannula, sized and modified as discussed herein to insert relatively tightly into clearance 34. Form 100 has a slot 102 formed therein with an open end 104 and a closed end 106. It may be noted that a shape of form 100 is complementary to a shape of clearance 34. Accordingly, when form 100 is inserted into clearance 34 it will substantially fill the same, with connecting wall 30 being received in open ended slot 102.

Figure 7:
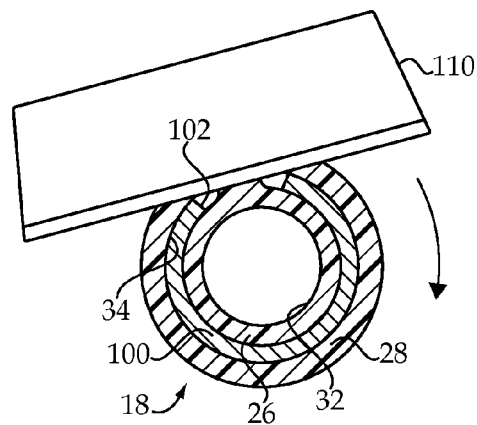
FIG. 7 is a sectioned view through an assembly of the form and extrusion of FIGS. 5 and 6, at yet another stage of making a balloon catheter.

Referring also now to FIG. 6, there is shown form 100 having been inserted into extrusion 18, and where the insertion has been stopped at an insertion depth via contacting closed end 106 to connecting wall 30. Slot 102 therefore extends into extrusion 18 about connecting wall 30. Also shown in FIG. 6 is a cutting blade 110 shown as it might appear just prior to being used to cut extrusion 18 so as to detach a portion of outer tubular wall 28. Referring also to FIG. 7, there is shown extrusion 18 where blade 110 is commencing cutting circumferentially through outer tubular wall 28. At the state shown in FIG. 7, a depth of the cutting is being limited via contacting blade 110 to form 100. Blade 110 may be rotated relative extrusion 18 to form a circumferential cut through outer tubular wall 28. The contact with form 100 may limit a depth of the circumferential cutting to outer tubular wall 28, preventing blade 110 from cutting into material of inner tubular wall 26.

Figure 8:
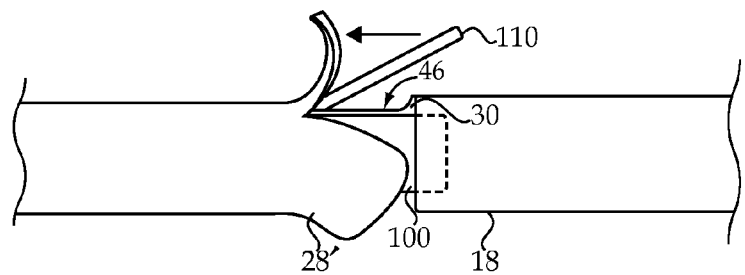
FIG. 8 is a side diagrammatic view of the assembly at yet another stage of making a balloon catheter.
Figure 9:
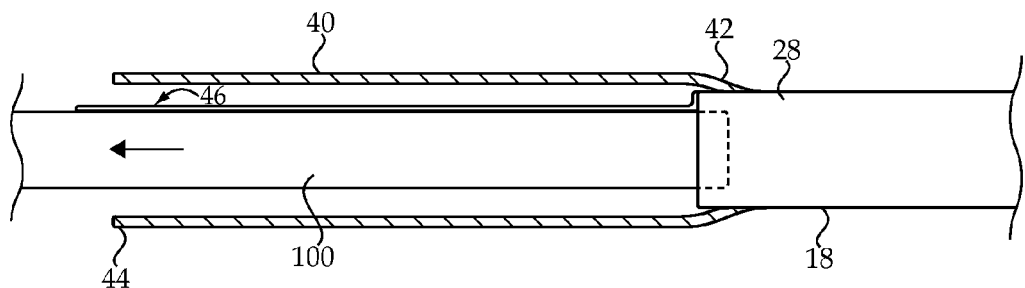
FIG. 9 is a partially sectioned side diagrammatic view of a balloon attached to the assembly, at yet another stage of making a balloon catheter.

Referring also now to FIG. 8, there is shown blade 110 after having formed a circumferential cut through outer tubular wall 28, and in the process of forming a longitudinal cut through wall 30. At the stage depicted in FIG. 8, blade 110 is being held at an angle to the axis of extrusion 18 and pushed longitudinally relative extrusion 18, in contact with form 100 upon opposite longitudinal sides of slot 102. Such contact may limit a depth of the longitudinal cutting to connecting wall 30, preventing blade 110 from cutting into inner tubular wall 26, and such that the cutting reduces a height of connecting wall 30 between the circumferential cut and the distal end of extrusion 18. In a manner generally discussed above, reducing the height of wall 30 may include reducing the height so as to leave longitudinally extending planar surface 46 upon extrusion 18 between the circumferential cut and the distal extrusion end. It will thus be appreciated that a segment 28' of outer tubular wall 28 is detached from extrusion 18, and may be discarded. Referring also now to FIG. 9, there is shown extrusion 18 as it might appear with form 100 still inserted, where surface 46 is visible just slightly above a profile of form 100. Proximal end 42 of balloon 40 has been attached to outer tubular wall 28. Form 100 may subsequently be withdrawn, to expose inner tubular wall 26, and distal end 44 of balloon 40 may be then attached to inner tubular wall 26. It will thus be understood that the attachment of balloon 40 will provide an enclosed cavity within balloon 40 in fluid communication with clearance 34, which can now be understood as forming an inflation lumen. The attachment of balloon 40 may further be such that wire guide lumen 32 and inner tubular wall 26 extend longitudinally through balloon 40. Prior to or subsequent to attaching balloon 40, manifold 12 may be attached and construction of balloon catheter 10 is substantially complete.

As alluded to above, prior balloon catheter construction methods commonly included attaching multiple elongate tubular elements via melting material of the tubular elements together and/or using adhesives. In the present disclosure, catheter 10 may be free of such adhesives and melt formed material, except where balloon 40 and manifold 12 attach to extrusion 18. Not only is construction simplified from the standpoint of materials, but also from the standpoint of labor time. The use of form 100 enables the cutting to be precise and reliable. While the present description and drawings depict forming the circumferential cut prior to the longitudinal cut, it will be appreciated that these steps might be reversed.

The present description is for illustrative purposes only, and should not be construed to narrow the breadth of the present disclosure in any way. Thus, those skilled in the art will appreciate that various modifications might be made to the presently disclosed embodiments without departing from the full and fair scope and spirit of the present disclosure. Other aspects, features and advantages will be apparent upon an examination of the attached drawings and appended claims.

What is claimed is:

1. A method of making a balloon catheter comprising the steps of:
    holding a one-piece extrusion including an inner tubular wall, an outer tubular wall extending circumferentially around the inner tubular wall, and a longitudinally extending connecting wall attaching the inner and outer tubular walls;
    cutting circumferentially through the outer tubular wall and longitudinally through the connecting wall so as to detach a portion of the outer tubular wall from the one-piece extrusion such that the outer tubular wall terminates at an axial end surface, and the inner tubular wall extends distally past the axial end surface; and
    attaching a proximal end of a balloon to a portion of the outer tubular wall that is different from the axial end surface, and a distal end of the balloon to the inner tubular wall after detaching the portion, and such that a first lumen formed by both the inner and outer tubular walls is in fluid communication with the balloon for inflating the same, and a second lumen formed by the inner tubular wall extends longitudinally through the balloon for guiding the balloon catheter over a wire guide.

2. The method of claim 1 further comprising the steps of inserting an elongate hollow form into a clearance between the inner tubular wall and the outer tubular wall, and limiting a depth of the cutting via contacting a blade in the cutting step with the elongate hollow form.

3. The method of claim 2 wherein the step of limiting further includes limiting a depth of the circumferential cutting to the outer tubular wall and limiting a depth of the longitudinal cutting to the connecting wall.

4. The method of claim 2 further comprising a step of reducing a height of the connecting wall via the longitudinal cutting, between the circumferential cut and a distal end of the one-piece extrusion.

5. The method of claim 4 wherein the step of reducing the height further includes reducing the height so as to leave a longitudinally extending planar surface upon the one-piece extrusion between the circumferential cut and the distal end.

6. The method of claim 2 further comprising a step of withdrawing the form subsequent to attaching the proximal end of the balloon and prior to attaching the distal end of the balloon.

7. The method of claim 1 wherein the exposed axial end of the outer tubular wall is positioned within the balloon.

8. The method of claim 1 wherein the second lumen has a circular profile; and the first lumen has a C-shaped profile that is coaxial with the circular profile.

9. The method of claim 1 wherein the connecting wall spans an angle between 10 degrees and 45 degrees about a center of the second lumen.

10. The method of claim 1 wherein the circumferential cutting and the longitudinal cutting occur in planes perpendicular to each other.

11. A method of making a balloon catheter comprising the steps of:

holding a one-piece extrusion including an inner tubular wall, an outer tubular wall extending circumferentially around the inner tubular wall, and a longitudinally extending connecting wall attaching the inner and outer tubular walls;

cutting circumferentially through the outer tubular wall and longitudinally through the connecting wall so as to detach a portion of the outer tubular wall from the one-piece extrusion;

attaching a proximal end of a balloon to the outer tubular wall and a distal end of the balloon to the inner tubular wall after detaching the portion, and such that a first lumen formed by both the inner and outer tubular walls is in fluid communication with the balloon for inflating the same, and a second lumen formed by the inner tubular wall extends longitudinally through the balloon for guiding the balloon catheter over a wire guide;

inserting an elongate hollow form into a clearance between the inner tubular wall and the outer tubular wall, and limiting a depth of the cutting via contacting a blade in the cutting step with the elongate hollow form; and receiving the connecting wall in an open-ended slot in the inserted form.

12. The method of claim 11 further comprising a step of stopping the insertion of the form via contacting a closed end of the slot with the connecting wall.

13. The method of claim 11 wherein the step of limiting further includes contacting the blade with the elongate hollow form upon opposite longitudinal sides of the slot during the step of cutting.

\* \* \* \* \*